(12) United States Patent
Zheng

(10) Patent No.: US 9,717,460 B2
(45) Date of Patent: Aug. 1, 2017

(54) SMART PHONE HAVING FUNCTIONS OF DIAGNOSING AND TREATING ILLNESS

(71) Applicant: Mingde Zheng, Beijing (CN)

(72) Inventor: Mingde Zheng, Beijing (CN)

(*) Notice: Subject to any disclaimer, the term of this patent is extended or adjusted under 35 U.S.C. 154(b) by 0 days.

(21) Appl. No.: 15/348,811

(22) Filed: Nov. 10, 2016

(65) Prior Publication Data

US 2017/0128017 A1 May 11, 2017

(30) Foreign Application Priority Data

Nov. 10, 2015 (CN) .......................... 2015 1 0755618

(51) Int. Cl.

| | |
|---|---|
| *A61B 5/02* | (2006.01) |
| *A61B 5/00* | (2006.01) |
| *A61H 39/00* | (2006.01) |
| *A61N 1/02* | (2006.01) |
| *A61B 5/0205* | (2006.01) |
| *A61N 1/36* | (2006.01) |
| *A61B 5/021* | (2006.01) |
| *A61B 5/024* | (2006.01) |

(Continued)

(52) U.S. Cl.
CPC .......... *A61B 5/6898* (2013.01); *A61B 5/0205* (2013.01); *A61B 5/4836* (2013.01); *A61B 5/6815* (2013.01); *A61B 5/7282* (2013.01); *A61B 5/7435* (2013.01); *A61B 5/7475* (2013.01); *A61H 39/002* (2013.01); *A61N 1/025* (2013.01); *A61N 1/36014* (2013.01); *A61B 5/021* (2013.01); *A61B 5/02438* (2013.01); *A61B 5/053* (2013.01); *A61B 5/14532* (2013.01); *A61B 5/14542* (2013.01); *A61B 2562/227* (2013.01); *A61H 2230/045* (2013.01); *A61H 2230/065* (2013.01); *A61H 2230/203* (2013.01); *A61H 2230/208* (2013.01); *A61H 2230/655* (2013.01)

(58) Field of Classification Search
None
See application file for complete search history.

(56) References Cited

U.S. PATENT DOCUMENTS

| | | | | |
|---|---|---|---|---|
| 4,852,570 | A * | 8/1989 | Levine | A61B 5/0205 128/906 |
| 2011/0046688 | A1 * | 2/2011 | Schwibner | A61N 1/39 607/5 |

(Continued)

*Primary Examiner* — Ankit D Tejani
(74) *Attorney, Agent, or Firm* — Kwan & Olynick LLP

(57) ABSTRACT

Smart phones capable of detecting electrical impedances of and providing electronic pulse stimuli to acupuncture points located on a human body are disclosed. An example smart phone is equipped with a hardware diagnosis module and a hardware treatment module that function based on the principle of holography of protruding parts of the human body, in addition to having regular smart phone functions. The diagnosis module may receive electrical impedance data detected from protruding parts of a human body and determine the type of illness according to the analog electrical impedance data. The treatment module may generate electronic pulse stimuli on acupoints located on the human body (such as ears, hands and feet), thereby performing electronic acupuncture treatment. The example smart phone may also detect blood pressure, heart rate, blood oxygen value and blood glucose values of the human body.

18 Claims, 4 Drawing Sheets

(51) Int. Cl.
*A61B 5/053* (2006.01)
*A61B 5/145* (2006.01)

(56) References Cited

U.S. PATENT DOCUMENTS

| | | | | |
|---|---|---|---|---|
| 2011/0093030 A1* | 4/2011 | Goetz | .................. | A61N 1/0553 607/17 |
| 2013/0204085 A1* | 8/2013 | Alexander | ............... | A61B 1/05 600/109 |
| 2014/0303452 A1* | 10/2014 | Ghaffari | .................. | A61B 1/05 600/301 |

* cited by examiner

SMART PHONE HAVING FUNCTIONS OF DIAGNOSING AND TREATING ILLNESS

RELATED APPLICATION

This application claims priority to the Chinese patent application no.: 201510755618.3, filed on Nov. 10, 2015, entitled "Smart Phone Having Functions of Diagnosing and Treating Illness," which is hereby incorporated by reference in its entirety.

TECHNICAL FIELD

Embodiments of the present disclosure relate to the technical field of hardware communication devices, and more particularly, to a smart phone equipped with hardware components for detecting electrical impedances of and providing electronic pulse stimuli to acupuncture points located on a human body.

BACKGROUND

According to holographs of human bodies, every protruding part of a human body (especially ears, hands, and feet) is an epitome of the human body, which contains all the physiological information and pathological information of the human body.

Acupoints (acupuncture points) corresponding to organs inside a human body are located in an ordered sequence on the protruding parts (such as ears, hands and feet) of the human body. Locations of acupoints of a human body are generally known and do not vary from person to person. Also generally known is that the resistance of those acupoints on lesions is relatively low. Electronic pulse currents can automatically flow to the acupoints with low resistance, automatically locate the acupoints corresponding to the lesions, and perform diagnosis of and treatment on the human body. As such, human illness can be diagnosed by detecting electrical impedance of acupoints on the protruding parts of the body; likewise, electronic holographic acupuncture treatment can be provided on the corresponding protruding parts and acupoints of the patient.

One of the popular mobile electronic devices users carry with them on their persons these days is a smartphone. There is therefore a need to provide a multi-functional smart phone that is capable of functioning as a smart phone as well as detecting electrical impedances of and providing electronic pulse stimuli to acupuncture points located on a human body.

Figure 1:
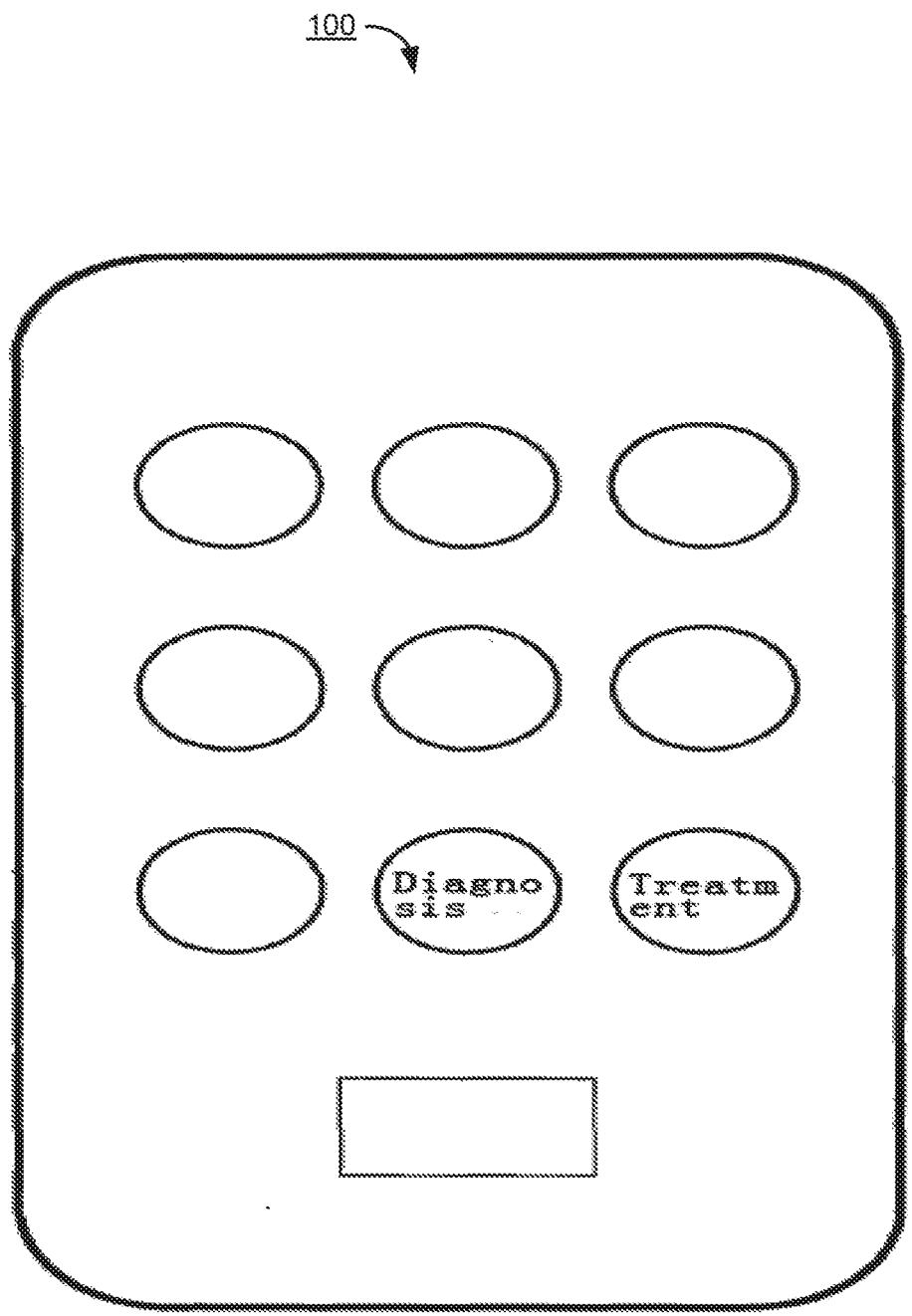
FIG. 1 is an exemplary diagram illustrating an example keypad of a smart phone capable of detecting electrical impedances of and providing electronic pulse stimuli to acupuncture points located on a human body.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The present disclosure provides systems and methods for using a smartphone to detect electrical impedances of and provide electronic pulse stimuli to acupuncture points located on a human body.

An object of embodiments of the present disclosure is to provide a smart phone having functions of diagnosing and treating illness, so as to address an issue of the current smart phone not having capabilities of facilitating improvement of personal health, so that not only can people enjoy modern life with convenience brought by smart phones in daily life, but they can also check their own health state (illness diagnosis) readily in daily life and maintaining their health state (electronic holographic acupuncture illness treatment).

According to an aspect of the embodiments of the present disclosure, there is provided a smart phone having functions of diagnosing and treating illness. The smart phone is equipped with a first plughole for a diagnosis module and a second plughole for a treatment module, and includes a diagnosis module and a treatment module, respectively. The diagnosis module is connected to an external smart detecting device via the first plughole, receives from the external smart detecting device analog electrical impedance data detected from protruding parts of a human body, and determines the type of illness according to the analog electrical impedance data. The treatment module produces electronic pulse for treatment, which is output to external therapeutic electrodes via the second plughole, and electronic pulse stimuli is generated on the acupoints on the protruding parts of the body (such as ears, hands and feet) as well as other parts of the human body, to achieve the goal of treating illness.

Optionally, the diagnosis module is connected to a smart electrical impedance probe for acupoints on human ears via the first plughole, and receives illness diagnosing electrical impedance data obtained by the smart electrical impedance probe from the acupoints on ears. Before diagnosis is made, a reference electrical impedance data for acupoints on ears should first be collected with the smart electrical impedance probe for acupoints on human ears as reference data for diagnosis and be stored in the diagnosis module.

Optionally, the diagnosis module is connected to an external detecting device via the first plughole, receives an analog signal of illness detecting data detected by the external detecting device, converts the analog signal of illness detecting data into an internal testing data in a designated format, and determines the type of illness according to internal testing data.

Optionally, the diagnosis module compares the internal testing data with a preset reference data for illness diagnosis, and determines the type of illness based on the comparison result.

Optionally, the treatment module produces therapeutic electronic pulse and outputs the therapeutic electronic pulse to the external therapeutic electrodes via the second plughole to generate a corresponding treatment waveform;

wherein said treatment waveform is any one of composite waveforms including continuous waves, intermittent waves and density-waves.

Optionally, the treatment module further receives a strength adjustment command for the output therapeutic electronic pulse, and adjusts the strength of the output therapeutic electronic pulse according to the strength adjustment command.

Optionally, the smart phone further comprises a power supply module and a phone module, the power supply module supplies power to other modules of the smart phone, and the phone module manipulates and controls the diagnosis module and the treatment module through a software application or an app installed on the smart phone for diagnosing and treating illness.

The smart phone having functions of diagnosing and treating illness provided in the embodiments of the present disclosure can diagnoses illness a patient has by detecting a value of electrical impedance at an acupoint on the ear, making use of the principle of holography of protruding parts of the human body. It can also obtain blood pressure, heart rates, blood oxygen levels and blood glucose levels of the human body through corresponding external measuring devices for measuring such purposes, providing people with basis for treating illness and health care. In addition, through the use of composite electronic pulses beneficial to the human body, composite waveforms such as continuous waves, intermittent waves and density-waves are used to stimulate acupoints on protruding parts of the body (ears, hands and feet) and on those on other parts of the body, to achieve healing effects.

Additional details of implementations are now described in relation to the Figures.

FIG. 1 is an exemplary diagram illustrating an example keypad 100 of a smart phone capable of detecting electrical impedances of and providing electronic pulse stimuli to acupuncture points located on a human body.

As shown in FIG. 1, in an operating interface (e.g., the keyboard 100) of a smart phone having functions of diagnosing and treating illness, an application software for diagnosing illness is started with a selection of an item "diagnosis" and an application software for treating illness is started with a selection of an item "treatment".

Figure 2:
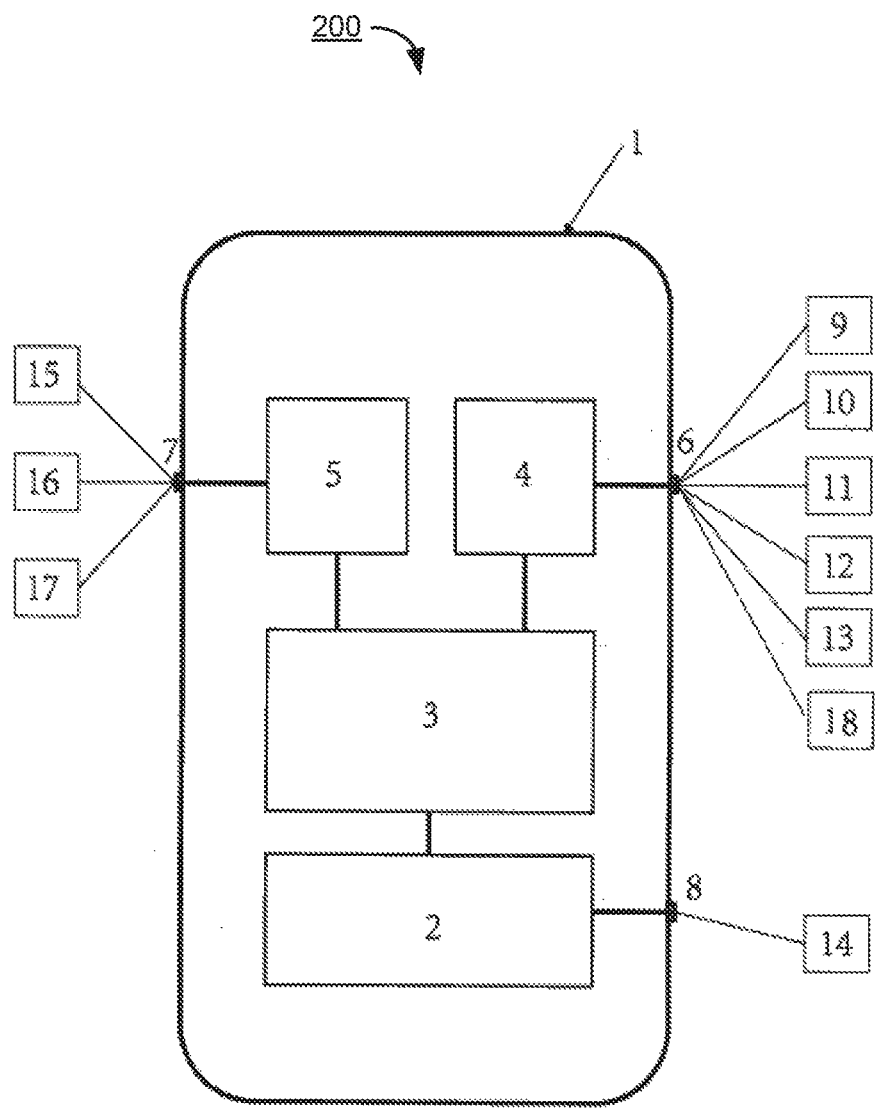
FIG. 2 is a structural view illustrating an example smart phone capable of detecting electrical impedances of and providing electronic pulse stimuli to acupuncture points located on a human body.

FIG. 2 is a structural view illustrating an example smart phone 200 capable of detecting electrical impedances of and providing electronic pulse stimuli to acupuncture points located on a human body.

As shown in FIG. 2, the smart phone 1 includes a power supply module 2, a phone module 3, a diagnosis module 4 and a treatment module 5. Below, descriptions on the modules in the above smart phone will be given.

The power supply module 2 supplies power to all the modules in the smart phone 1, and may be formed with lithium-ion batteries having protection abilities during charging to meet requirements of operating normally for a long period of time.

The phone module 3 is protected with electro-magnetic compatibility (EMC), on which application software for diagnosing and treating illness is installed in addition to regular functions of a smart phone. Through the phone module 3, commands can be generated and sent to the corresponding modules in the smart phone 1, especially the diagnosis module 4 and the treatment module 5, and information and data is displayed. By connecting with the diagnosis module 4 and the treatment module 5, the phone module 3 performs control over the operations of the diagnosis module 4 and the treatment module 5. Also, the phone module 2 is connected with the power supply module 2 as well, which is equipped with a charging plughole 8 to connect to a charger 14 for power charging.

The diagnosis module 4 is constructed based on the principle of holography of protruding parts of the human body and implemented with detecting methods for blood pressure, heart rates, blood oxygen levels and blood glucose levels. It is installed with a hybrid integrated circuit of a single chip microcomputer having an EMC protection ability, the size of which fits with that of a regular smart phone. The phone module 3 performs data exchange with the hybrid integrated circuit through a physical connection cable, and utilizes the application software for diagnosing and treating illness to control the hybrid integrated circuit. The diagnosis module 4 is connected to an external smart detecting device via a first plughole, and receives illness detection data detected by the external smart detecting device. It then determines the type of illness according to the illness detection data. Preferably, the diagnosis module 4 is connected to a smart electrical impedance probe for acupoints on human ears via the first plughole, and receives electrical impedance data on the acupoints on ears for illness diagnosis detected by the smart electrical impedance probe for acupoints on human ears. Before diagnosis is made, a reference electrical impedance data for acupoints on ears should first be collected with the smart electrical impedance probe for acupoints on human ears and set as reference data for diagnosis. In addition, the diagnosis module 4 can be connected with other external smart detecting device via the first plughole, including but not limited to, a device for detecting blood pressure, a device for detecting heart rates, a device for detecting blood oxygen levels, or a device for detecting blood glucose levels, etc.

In an optional embodying mode, signals detected by the external device for detecting blood pressure/heart rates/blood oxygen levels/blood glucose levels or the electrical impedance probe for acupoints on human ears are transmitted to the diagnosis module 4 after being converted via an extended socket such as a micro-USB socket of the smart phone 2. The signals are then converted into internal testing data, based on which illness is diagnosed by the application software for diagnosing and treating illness, and the detected blood pressure/heart rates/blood oxygen levels/blood glucose levels or electrical impedance data on the probed acupoints are displayed on the screen of the smart phone 1. For example, data collection can be done using a typical general use electronic blood pressure collection probe, the collected data signals of blood pressure in an analog form may be converted into a digital form and the collected data signals in the digital form are sent to the diagnosis module 4, which then converts the collected data in the digital form into its internal testing data. The internal testing data is different from typical digital data to indicate that the internal testing data is to be processed by the diagnosis module 4, for example, adding a proper mark or identifier to the digital data after its A/D conversion or adjusting a sequence of digital data after the A/D conversion. Likewise, collection and processing of heart rates/blood oxygen levels/blood glucose levels or the electrical impedance data of acupoints and the like may be done in a similar fashion (i.e. the A/D conversion method or a counting method).

Take detection of blood pressure as example. After an external smart device for detecting blood pressure is connected, if the internal testing data after conversion indicates detected systolic reading of 18.9 Kpa and a diastolic reading of 12.9 Kpa, higher than a standard reading of normal blood pressure, systolic 18.7 Kpa and diastolic 12.0 Kpa, then the person being tested is warned of being suspected of having high blood pressure.

In the process of illness diagnosis, the item "diagnosis" on the operating interface of the smart phone 1 is selected, and the plug of a contact probe 9 is connected with a first plughole 6 via a cable, forming a circuit for diagnosis. A first person performing the diagnosis operation first collects a reference value on a reference acupoint of a second person being tested by placing the contact probe 9 between a highest point on the upper end of the earlobe and a middle finger of the second person, and pre-stores the reference value in the diagnosis module. Then, the first person holds the contact probe 9, evenly presses it and moves it along the acupoints on the ear of the second person, staying a proper duration such as 1 or 2 seconds. When the contact probe 9 detects an electrical impedance data of an acupoint, the detected electrical impedance data is compared against the pre-stored reference value to determine whether there are lesions in the organs or issues corresponding with the accupoint. For example, if during probing the contact probe 9 gives out an alarm sound at an acupoint in the ear cavity, then the person being tested may be warned of a possible heart disease.

The phone module 3 receives a feedback information (diagnosing results) from the diagnosis module 4, and presents a notification of the diagnosing results (such as an alarm indicating a positive diagnosis result of an illness) by using a display or audio function of the phone module 3. If no alarm is given, a diagnosis result indicates that the part of the body corresponding with the acupoint at which an electrical impedance data is detected is normal. It is desirable to have both ears probed, since lesions on the left side of the body are typically reflected on the left ear and those on the right side of the body are typically reflected on the right ear. The illness diagnosing operations can be automatically stopped when such software function is turned off in the application software for diagnosing and treating illness in the phone module 3. The diagnosis module 4 then enters into a sleep mode to save battery power.

When blood pressure, heart rates, blood oxygen levels or blood glucose levels are measured, the "diagnosing" item is selected in the operating interface of the smart phone 1, then a menu item such as "blood pressure" (or heart rates, or blood oxygen levels or blood glucose levels, or electrical impedance of acupoint) function is selected. Accordingly, the plug of the electronic blood pressure probe 10 (or electronic heart rate probe 11, or electronic blood oxygen level probe 12, or electronic blood glucose probe 13, or probe 18 for electrical impedance of acupoint) is connected with the first plughole 6, forming a probing circuit to perform probe. The diagnosis module 4 performs illness diagnosis according to data obtained from probing, the phone module 3 receives feedback information (diagnosis result data) from the diagnosis module 4, and a diagnosis notice is given utilizing the display and audio function of the phone module 3.

The treatment module 5 has a hybrid integrated circuit based on a module of a single-chip microcomputer designed according to the principle of holography of protruding parts of the human body, and the size of the hybrid integrated circuit meets the size requirements of a regular smart phone. The phone module 3 performs data exchange with the hybrid integrated circuit via an internal physical connection cable, and performs control over the hybrid integrated circuit using the application software for diagnosing and treating illness. The treatment module 5 is connected with the second plughole 7 through an electric cable. When performing illness treatment, a "treatment" item is selected in the operating interface of the smart phone 1, and a plug for ear therapeutic electrodes 15, body therapeutic electrodes 16, hand therapeutic electrodes or foot therapeutic electrodes 17 is connected with the second plughole 7 (typically a standard port, such as Micro-USB) through an electric cable, forming a circuit for treatment/therapy. The treatment module 5 produces a therapeutic electronic pulse which is output to external therapeutic electrode, thereby achieving treatment functions for various illnesses through electronic acupuncture. For example, if a diagnosis result by the diagnosis module 4 indicates that the person being tested has high blood pressure, then therapeutic electrodes for ears, hands and/or feet may respectively be attached to electrode patches on acupoints on ears, hands and/or feet to perform electronic pulse therapy to selected Sanyinjiao acupoints, fengchi acupoints and/or taichong acupoints, etc.

The treatment module 5 may be implemented with a built-in single chip microcomputer, and is controlled to produce electronic pulse when a therapeutic pulse control command is received from the application software for diagnosing and treating illness. The electronic pulse is then output to therapeutic electrodes placed on the body via an extended port after being amplified to a designated strength, producing therapeutic effects. Waveforms achieving treatment may be composite waveforms such as continuous waves, intermittent waves and density-waves.

According to a corresponding device with application software for diagnosing and treating illness, strengths of outputs from the electrodes may be adjusted in the treatment module 5. After a command for adjusting strength of the electronic pulse is received, the strength of the output electronic pulse is adjusted accordingly. The user may slowly adjust the strength of the output electronic pulse (to the extent of having tingling sensations and feeling comfortable desirably), by manipulating symbols like "+/−" on the interface of the application software for diagnosing and treating illness. The user may press "+/−" symbols to first have a current value displayed, and then press "+" to gradually enhance the strength or press "−" to gradually reduce the strength. The composite electronic pulse produced by the single chip microcomputer of the treatment module 5 is output through an amplifying circuit, and performs electronic acupuncture treatment to acupoints on the protruding parts or on lesion parts of the body. During treatment/therapy, treating time duration may be adjusted with the application software for diagnosing and treating illness. When time duration is adjusted, the application software for diagnosing and treating illness displays a current time duration and an adjusting button on the phone screen, and the user may press the "+/−" button to complete time adjustment. Electronic acupuncture is performed through the smart phone 1, thereby achieving treatment and therapeutic effects. After a treatment time duration times out or is stopped manually, the treatment module enters into a sleeping mode to save battery power.

Figure 3:
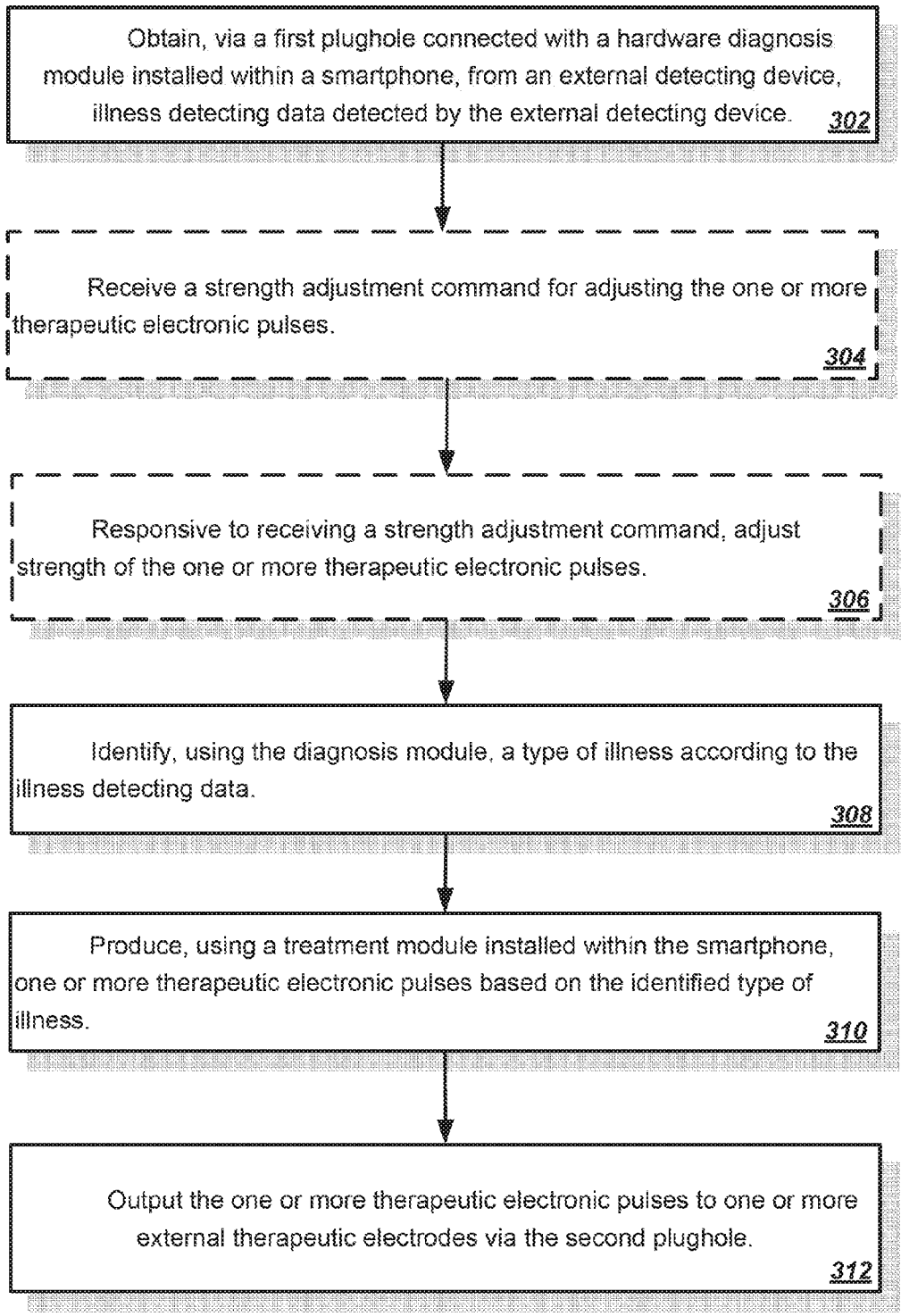
FIG. 3 is a flow chart illustrating an embodiment of a method for detecting electrical impedances of and providing electronic pulse stimuli to acupuncture points located on a human body.

FIG. 3 is a flow chart illustrating an embodiment of a method 300 for detecting electrical impedances of and providing electronic pulse stimuli to acupuncture points located on a human body.

The method 300, in some implementations, include obtaining (302), via a first plughole connected with a hardware diagnosis module installed within a smart phone, from an external detecting device, illness detecting data detected by the external detecting device. The method 300 further include identifying (308), using the diagnosis module, a type of illness according to the illness detecting data.

The method 300, in some implementations, may also include: producing (310), using a treatment module installed within the smart phone, one or more therapeutic electronic pulses based on the identified type of illness.

The strength of the therapeutic electronic pulses may be adjusted. The method 300, in some implementations, include receiving (304) a strength adjustment command for adjusting the one or more therapeutic electronic pulses; and responsive to receiving a strength adjustment command, adjusting (306) strength of the one or more therapeutic electronic pulses.

The method 300, in some implementations, include may also include: outputting (312) the one or more therapeutic electronic pulses to one or more external therapeutic electrodes via the second plughole.

The method 300, in some implementations, may include: obtaining electrical impedance data detected by an electrical impedance probe. The electrical impedance probe may be connected with the diagnosis module via the first plughole; and the electrical impedance probe is configured to be attachable to an acupoint located on a human ear, for exampling, the electrical impedance probe may have a similar contour to that of a human ear or may be made of materials (e.g., silicon or plastic) that are suitable to be attached to a human ear without causing discomfort.

The method 300, in some implementations, may include: obtaining an analog signal of illness detecting data detected by the external detecting device; converting the analog signal of illness detecting data into an internal testing data having a designated format; and determining the type of illness according to the internal testing data.

The method 300, in some implementations, may include: comparing the internal testing data with a predetermined reference data for illness diagnosis; and identifying the type of illness based on the comparing.

The method 300, in some implementations, may include: generating a treatment waveform based on which the one or more therapeutic electronic pulses are produced, wherein the treatment waveform is one of a continuous wave, an intermittent wave, and a density wave.

The method 300, in some implementations, may include: receiving a strength adjustment command for adjusting the one or more therapeutic electronic pulses; and responsive to receiving a strength adjustment command, adjusting strength of the one or more therapeutic electronic pulses.

In some implementations, the smart phone comprises a power supply module and a phone module, wherein the power supply module supplies power to the smart phone, and the phone module controls the diagnosis module and the treatment module through a software application installed on the smart phone.

In some implementations, the smart phone further comprises a touchscreen display; and the method 300 optionally includes presenting the illness detecting data on the touchscreen display.

In some implementations, the second plughole of the smart phone includes a Micro-USB port.

In some implementations, the treatment module includes a hybrid integrated circuit; and the external detecting device includes one of a device for detecting blood pressure, a device for detecting heart rates, a device for detecting blood oxygen levels, or a device for detecting blood glucose levels.

Figure 4:
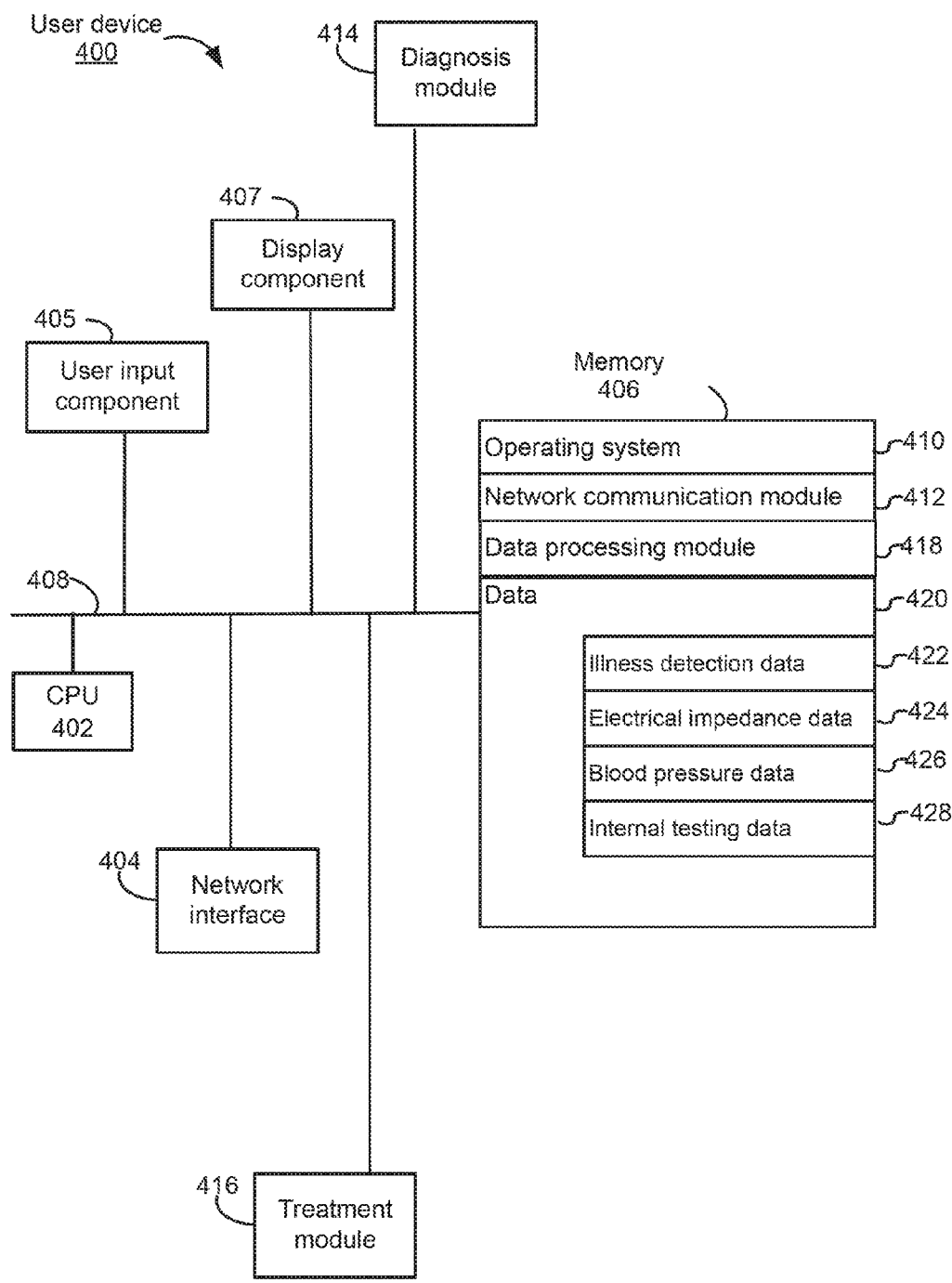
FIG. 4 is a schematic view illustrating an embodiment of a smart phone.

FIG. 4 is a schematic view illustrating an embodiment of a user device (e.g., a smart phone) 400, which can be the device 200 shown in FIG. 2. The device 400 in some implementations includes one or more processing units CPU(s) 402 (also referred to as hardware processors), one or more network interfaces 404, a memory 406, and one or more communication buses 406 for interconnecting these components. The communication buses 406 optionally include circuitry (sometimes called a chipset) that interconnects and controls communications between system components. The memory 406 typically includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. The memory 406 optionally includes one or more storage devices remotely located from the CPU(s) 402. The memory 406, or alternatively the non-volatile memory device(s) within the memory 406, comprises a non-transitory computer readable storage medium. In some implementations, the memory 406 or alternatively the non-transitory computer readable storage medium stores the following programs, modules and data structures, or a subset thereof:

- an operating system 410, which includes procedures for handling various basic system services and for performing hardware dependent tasks;
- a network communication module (or instructions) 412 for connecting the device 400 with other devices (e.g. an external testing device, a human pulse measuring device, a blood sugar meaning device) via one or more plughole, data cables, and network interfaces 404 (wired or wireless);
- a data processing module 424 for processing testing test collected by the diagnosis module 414 and provide instructions to the treatment module 416 for generating one or more electrical stimuli; and
- data 414 stored on the device 400, which may include:
  - a first set of programming statements 416A (e.g., 10 lines of VB SCRIPT source code), which may include:
    - illness detection data 422 collected from one or more acupuncture points located on a human body;
    - electrical impedance data 424 collected from one or more acupuncture points located on a human body;
    - blood pressure data 426 collected from one or more acupuncture points located on a human body; and
    - internal testing data 428 converted from the illness detection data 422 by the data processing module 424.

The device 400 may include a diagnosis module 414 having technical functionalities and features described in the present disclosure. The device 400 may also include a treatment s module 416 having technical functionalities and features described in the present disclosure.

The device 400 may also include a user input component 407 for enabling a user to interact with (e.g., providing input to) the device 400. In some implementations, the user input component 407 may be a keyboard, a mouse, a touchpad, a track pad, or the touch screen 100. The device 400 may further include a display component 407 for presenting information, e.g., testing data, blood sugar information, or any other information, to a user.

In some implementations, one or more of the above identified elements are stored in one or more of the previously mentioned memory devices, and correspond to a set of instructions for performing functions described above. The above identified modules or programs (e.g., sets of instructions) need not be implemented as separate software programs, procedures or modules, and thus various subsets of these modules may be combined or otherwise re-arranged in various implementations. In some implementations, the memory 406 optionally stores a subset of the modules and data structures identified above. Furthermore, the memory 406 may store additional modules and data structures not described above.

Although FIG. 4 shows a "user device 400," FIG. 4 is intended more as functional description of the various features which may be present in computer systems than as a structural schematic of the implementations described herein. In practice, and as recognized by those of ordinary skill in the art, items shown separately could be combined and some items could be separated.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first plughole could be termed a second plughole, and, similarly, a second plughole could be termed a first plughole, without changing the meaning of the description, so long as all occurrences of the "first plughole" are renamed consistently and all occurrences of the "second plughole" are renamed consistently. The first plughole and the second plughole are both plugholes, but they are not the same plughole.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A smart phone, comprising:
   a hardware diagnosis module;
   a hardware treatment module;
   a first plughole connected with the diagnosis module;
   a second plughole connected with the treatment module;
   a non-transitory memory; and
   one or more hardware processors coupled to the non-transitory memory and configured to execute instructions to cause the system to perform operations comprising:
   obtaining, via the first plughole, from an external detecting device, illness detecting data detected by the external detecting device;
   identifying, using the diagnosis module, a type of illness according to the illness detecting data;
   producing, using the treatment module, one or more therapeutic electronic pulses based on the identified type of illness;
   outputting the one or more therapeutic electronic pulses to one or more external therapeutic electrodes via the second plughole; and
   generating a treatment waveform based on which the one or more therapeutic electronic pulses are produced, wherein the treatment waveform is a composite waveform of a continuous wave, an intermittent wave, and a density wave.

2. The smart phone of claim 1, wherein the operations further comprise:
   obtaining electrical impedance data detected by an electrical impedance probe;
   wherein the electrical impedance probe is connected with the diagnosis module via the first plughole; and
   wherein the electrical impedance probe is configured to be attachable to an acupoint located on a human ear.

3. The smart phone of claim 1, wherein the operations further comprise:
   obtaining an analog signal of illness detecting data detected by the external detecting device;
   converting the analog signal of illness detecting data into an internal testing data having a designated format; and determining the type of illness according to the internal testing data.

4. The smart phone of claim 3, wherein the operations further comprise:
comparing the internal testing data with a predetermined reference data for illness diagnosis; and
identifying the type of illness based on the comparing.

5. The smart phone of claim 1, wherein the operations further comprise:
receiving a strength adjustment command for adjusting the one or more therapeutic electronic pulses; and
responsive to receiving the strength adjustment command, adjusting strength of the one or more therapeutic electronic pulses.

6. The smart phone of claim 1, wherein the smart phone further comprises a power supply module and a phone module, wherein the power supply module supplies power to the smart phone, and the phone module controls the diagnosis module and the treatment module through a software application installed on the smart phone.

7. The smart phone of claim 1, wherein the smart phone further comprises a touchscreen display; and wherein the operations further comprise:
presenting the illness detecting data on the touchscreen display.

8. The smart phone of claim 1, wherein the second plughole includes a Micro-USB port.

9. The smart phone of claim 1, wherein the treatment module includes a hybrid integrated circuit; and the external detecting device includes one of a device for detecting blood pressure, a device for detecting heart rates, a device for detecting blood oxygen levels, or a device for detecting blood glucose levels.

10. A method comprising:
obtaining, via a first plughole connected with a hardware diagnosis module installed within a smart phone, from an external detecting device, illness detecting data detected by the external detecting device;
identifying, using the diagnosis module, a type of illness according to the illness detecting data;
producing, using a treatment module installed within the smart phone, one or more therapeutic electronic pulses based on the identified type of illness;
outputting the one or more therapeutic electronic pulses to one or more external therapeutic electrodes via the second plughole; and
generating a treatment waveform based on which the one or more therapeutic electronic pulses are produced, wherein the treatment waveform is a composite waveform of a continuous wave, an intermittent wave, and a density wave.

11. The method of claim 10, further comprising:
obtaining electrical impedance data detected by an electrical impedance probe;
wherein the electrical impedance probe is connected with the diagnosis module via the first plughole; and
wherein the electrical impedance probe is configured to be attachable to an acupoint located on a human ear.

12. The method of claim 10, further comprising:
obtaining an analog signal of illness detecting data detected by the external detecting device;
converting the analog signal of illness detecting data into an internal testing data having a designated format; and
determining the type of illness according to the internal testing data.

13. The method of claim 12, further comprising:
comparing the internal testing data with a predetermined reference data for illness diagnosis; and
identifying the type of illness based on the comparing.

14. The method of claim 10, further comprising:
receiving a strength adjustment command for adjusting the one or more therapeutic electronic pulses; and
responsive to receiving the strength adjustment command, adjusting strength of the one or more therapeutic electronic pulses.

15. The method of claim 10, wherein the smart phone comprises a power supply module and a phone module, wherein the power supply module supplies power to the smart phone, and the phone module controls the diagnosis module and the treatment module through a software application installed on the smart phone.

16. The method of claim 10, wherein the smart phone further comprises a touchscreen display; and further comprising:
presenting the illness detecting data on the touchscreen display.

17. The method of claim 10, wherein the second plughole includes a Micro-USB port.

18. The method of claim 10, wherein the treatment module includes a hybrid integrated circuit; and the external detecting device includes one of a device for detecting blood pressure, a device for detecting heart rates, a device for detecting blood oxygen levels, or a device for detecting blood glucose levels.

* * * * *